United States Patent
Ischdonat et al.

(10) Patent No.: US 7,249,491 B2
(45) Date of Patent: Jul. 31, 2007

(54) APPARATUS FOR MEASURING THE PERMEABILITY OF A CIRCULATING BAND IN A PAPER MACHINE

(75) Inventors: Thomas Ischdonat, Bachhagel (DE);
Ralf Pfifferling, Gerstetten (DE);
Rudolf Muench, Koenigsbronn (DE);
Michael Sollinger, Stuttgart (DE);
Wolfgang Ulfert, Tettnang (DE)

(73) Assignee: Voith Paper Patent GmbH, Heidenheim (DE)

( * ) Notice: Subject to any disclaimer, the term of this patent is extended or adjusted under 35 U.S.C. 154(b) by 321 days.

(21) Appl. No.: 10/942,385

(22) Filed: Sep. 16, 2004

(65) Prior Publication Data

US 2005/0092069 A1    May 5, 2005

(30) Foreign Application Priority Data

Sep. 19, 2003    (DE)    ................. 103 43 417

(51) Int. Cl.
*G01N 15/08* (2006.01)

(52) U.S. Cl. .............................................. 73/38

(58) Field of Classification Search .................. 73/38
See application file for complete search history.

(56) References Cited

U.S. PATENT DOCUMENTS

| | | | | |
|---|---|---|---|---|
| 3,762,211 A | * | 10/1973 | Poulsen | 73/38 |
| 4,880,499 A | * | 11/1989 | Pikulik | 162/198 |
| 4,991,425 A | | 2/1991 | Gulya et al. | 73/38 |
| 5,725,737 A | | 3/1998 | Pikulik et al. | 162/263 |
| 6,266,999 B1 | * | 7/2001 | Arnshav | 73/38 |
| 6,971,261 B2 | * | 12/2005 | Ischdonat et al. | 73/38 |
| 2005/0145358 A1 | * | 7/2005 | Ischdonat et al. | 162/199 |

* cited by examiner

*Primary Examiner*—Hezron Williams
*Assistant Examiner*—John Fitzgerald
(74) *Attorney, Agent, or Firm*—Taylor & Aust, P.C.

(57) ABSTRACT

An apparatus for measuring the permeability of a circulating band, in particular of a dewatering band in a papermaking machine, having a nozzle from which a measuring fluid flows onto the band. In order to avoid undesired lifting of the nozzle off the band due to pressure peaks, the apparatus according to the present invention has a nozzle which can be pressed onto the circulating band with a constant contact pressure.

10 Claims, 2 Drawing Sheets

APPARATUS FOR MEASURING THE PERMEABILITY OF A CIRCULATING BAND IN A PAPER MACHINE

BACKGROUND OF THE INVENTION

1. Field of the Invention

The present invention relates to an apparatus for measuring the permeability of a circulating band, in particular of a dewatering band in a papermaking machine, having a nozzle from which a measuring fluid flows onto the band.

2. Description of the Related Art

Permeability measurements on circulating bands generally have to be carried out with a high pressure of the measuring fluid in order that the stream of measuring fluid can penetrate the band. It is therefore necessary to press the nozzle correspondingly firmly against the band, since the volume flow of the measuring fluid produces a correspondingly high reaction force on the nozzle, and thus forces the nozzle away from the band. In particular, when pressure fluctuations occur in the volume flow of the measuring fluid, there is the risk that the nozzle is lifted off the band by the reaction force acting on it, which can result in an erroneous permeability measurement.

What is needed in the art is an improved apparatus where the nozzle is prevented from lifting off the band in the event of pressure peaks as a result of pressure fluctuations in the measuring fluid.

SUMMARY OF THE INVENTION

The present invention provides an apparatus for measuring the permeability of a circulation band where the nozzle is prevented from lifting off the band in the event of pressure peaks as a result of pressure fluctuations in the measuring fluid.

The present invention comprises, in one form thereof, an apparatus for measuring the permeability of a circulation band in which the nozzle can be pressed against the circulating band with a constant contact pressure. Consequently, pressure fluctuations in the measuring fluid can no longer affect the measuring accuracy of the apparatus, as a result of the always constant contact pressure of the nozzle against the circulating band. This is, in the widest sense, also a precondition for a plurality of measurements to be comparable with one another, in particular also with regard to various items of clothing and various plants.

The requisite contact pressure rises with the increasing exit pressure of the measuring fluid from the nozzle, with the band speed and with the band tension. It is therefore expedient if the contact pressure can be set as a function of the exit pressure of the measuring fluid from the nozzle and/or of the band speed and/or of the band tension. The contact pressure expediently corresponds at least to the nozzle exit pressure, in order to be able to carry out a permeability measurement that supplies fault-free and accurate measured results.

In a development of the present invention, the nozzle is integrated in a measuring head. This measuring head ensures a defined surface, with which the band is in contact during measurement. It additionally ensures that the nozzle is always placed on the felt in the same way. In order that the volume flow can best penetrate the band, it is expedient if the nozzle is positioned perpendicularly with respect to the band during the measurement. Devices for measuring the band speed, the nozzle exit speed and the nozzle exit pressure can be connected to the measuring head.

In order to be able to ensure optimum pressing of the nozzle against the band during the measurement, the measuring head can be pressed against the band with a specific contact pressure and/or the nozzle within the measuring head can additionally be pressed against the band independently of the contact pressure of the measuring head. The outlet opening of the nozzle in this case has a defined area. The nozzle is preferably configured in such a way that possible leakage losses are as low as possible.

In a specific embodiment, the measuring head can have a contact surface that can be pressed onto the band. In this way, the above described defined area is ensured during the measurement. In an alternative embodiment, however, it is also possible for the measuring head to be constructed as a frame. This construction also delimits the defined measuring area for the measurement.

In order to keep the frictional conditions between the measuring head and the circulating band as low as possible during the measurement, the frame can be provided with sliding rails and/or rollers. If the measuring head is fabricated from an abrasion-resistant material, in particular from a ceramic material, this has particularly long service life.

Depending on the size of the nozzle, the contact force required to produce the contact pressure can be provided with a specific safety margin. This safety margin for the contact pressure can lie in an interval from 1 to 20.

Particularly good pressing of the nozzle against the band is achieved if the contact pressure of the measuring head against the band lies in the range from 200 to 1500 N/m$^2$. If account is taken of the lowest possible friction at the highest possible band speed, then good measured results are achieved in particular with a contact pressure in the range from 400 to 800 N/m$^2$. In general, the contact pressure of the nozzle is much greater than the contact pressure of the measuring head.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
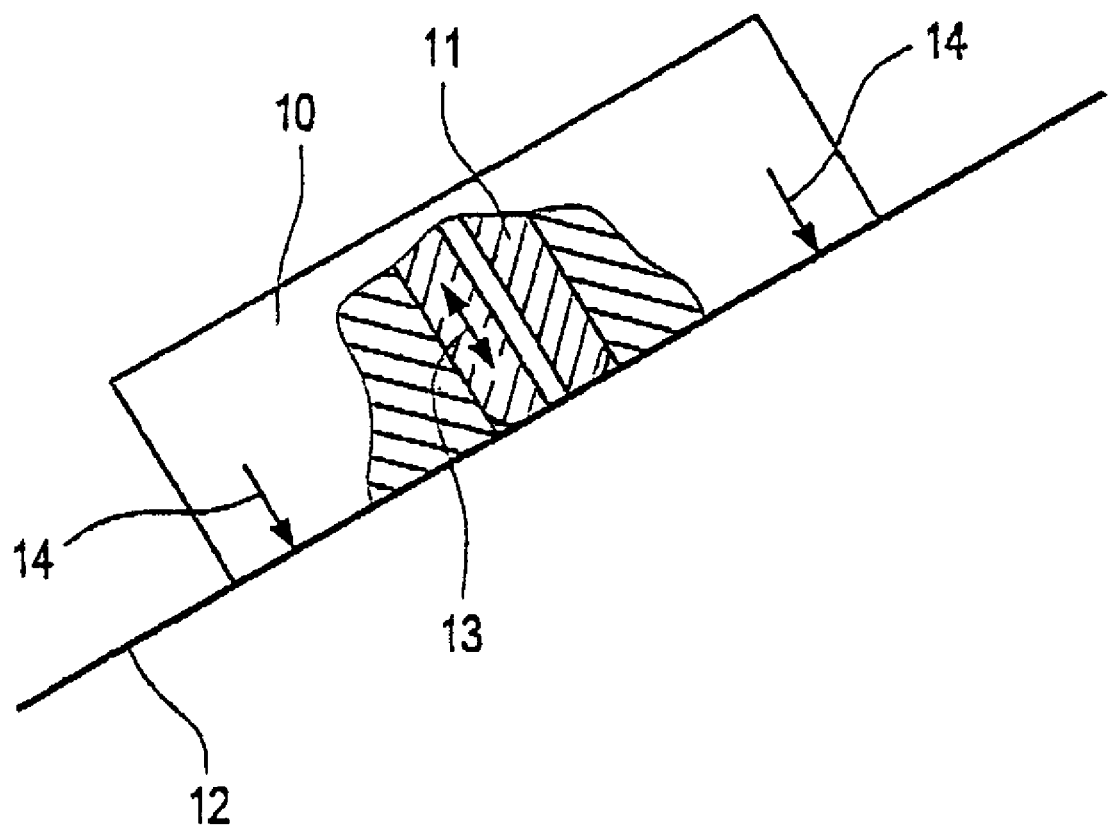
FIG. 1 is a side view with a partial section of a measuring head with nozzle.

Referring now to the drawings, and more particularly to FIG. 1, there is shown a measuring head 10, in which a nozzle 11 having a preferable nozzle opening diameter of 1 mm and having a preferable nozzle external diameter of 10 mm is arranged. A circulating band 12, which is a dewatering band of a papermaking machine, runs through under measuring head 10. A permeability measurement of band 12 is carried out by using measuring head 10 and nozzle 11. For this purpose, a volume flow of a measuring fluid provided with a high pressure is pressed through band 12 out of nozzle 11. On account of the high nozzle exit pressure of the measuring fluid, the high speed of band 12 and the high tension of the band, nozzle 11 must be pressed against the band 12 with the highest possible contact pressure. In order to ensure the maximum contact pressure of nozzle 11 against band 12, nozzle 11 is pressed against band 12 with a contact pressure illustrated by arrow 13. This contact pressure depends, inter alia, on the nozzle shape and on the band surface. Irrespective of the contact pressure 13 of nozzle 11, measuring head 10 is additionally pressed against band 12 by way of a contact pressure illustrated by arrows 14. This contact pressure preferably lies in a range from 200 to 1500 $N/m^2$. In this way, the maximum contact pressure of the nozzle 11 and measuring head 10 against band 12 can be ensured. Since nozzle 11 is arranged perpendicularly on band 12 for an optimum measured result, it is important that measuring head 10 is pressed firmly against band 12. This ensures that nozzle 11 is always placed perpendicularly on band 12.

Figure 2:
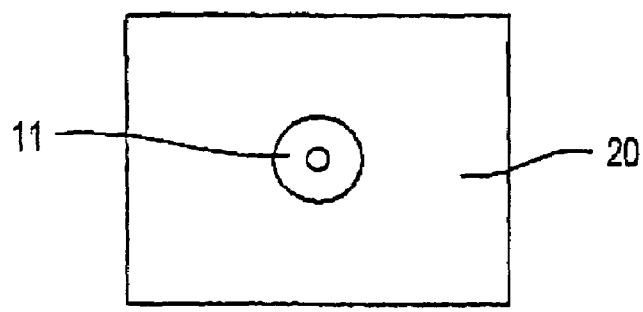
FIG. 2 is a plan view of a first embodiment of a measuring head.
Figure 3:
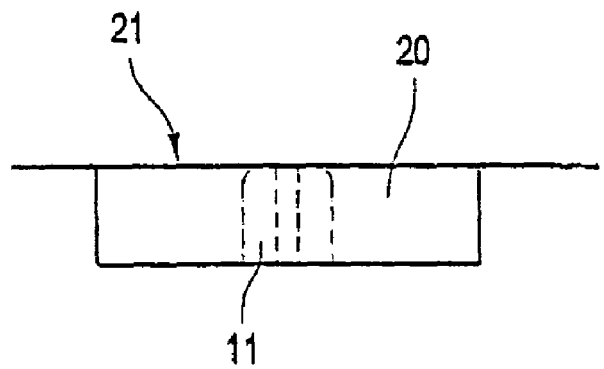
FIG. 3 is a side view of the measuring head from FIG. 1.

FIG. 2 shows a measuring head 20 in which a nozzle 11 is arranged. Measuring head 20 has a flat contact surface 21. During the measuring operation, measuring head 20 is placed with the flat contact surface 21 on band 12. The flat contact surface 21 ensures that nozzle 11 is always positioned perpendicularly with respect to band 12 during the measuring operation. In addition, the flat contact surface 21 forms a defined measuring area for the measuring operation.

Figure 4:
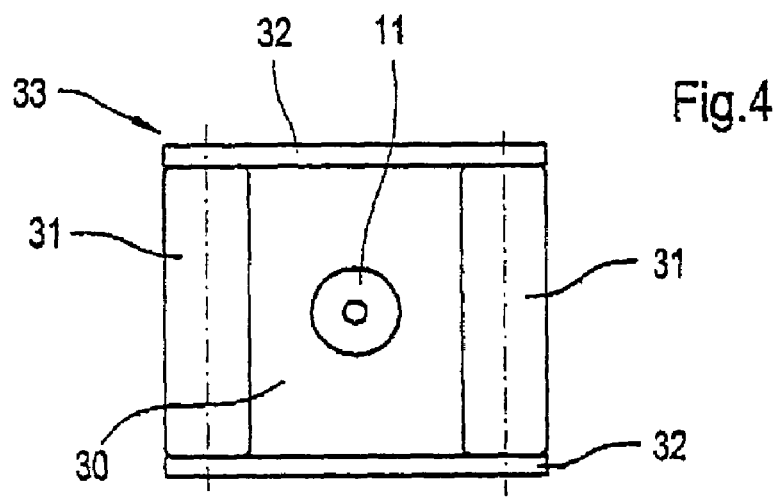
FIG. 4 is a plan view of a further embodiment of a measuring head.
Figure 5:
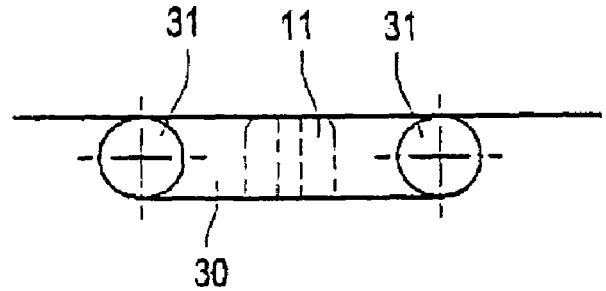
FIG. 5 is a side view of the measuring head from FIG. 4.

FIGS. 4 and 5 show a measuring head 30 which is provided with rollers 31 and nozzle 11. Rollers 31 are connected to one another by connecting elements 32. Rollers 31 and connecting elements 32 thus form a frame 33. Frame 33 forms a defined measuring area for the measurement operation. It additionally ensures that nozzle 11 is always pressed perpendicularly against band 12. During the measuring operation, rollers 31 are placed on band 12. As a result, low friction between measuring head 30 and band 12 is ensured. The contact pressure of measuring head 10, 20 and 30 can be set as a function of the nozzle exit pressure of the measuring fluid from nozzle 11, of the speed of band 12 and of the tension of band 12. In order to ensure a fault-free permeability measurement, care must be taken that the contact pressure corresponds at least to the nozzle exit pressure.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF DESIGNATIONS

10 Measuring head
11 Nozzle
12 Band
13 Arrow
14 Arrow
20 Measuring head
21 Contact surface
30 Measuring head
31 Roller
32 Connecting element
33 Frame

What is claimed is:

1. An apparatus for measuring the permeability of a circulating band in a papermaking machine, comprising: a nozzle from which a measuring fluid flows onto the circulating band, wherein said nozzle is be pressed onto the circulating band with a constant contact pressure, the circulating band being a dewatering band.

2. The apparatus of claim 1, further including an exit pressure associated with said measuring fluid from said nozzle and both a band speed and a band tension associated with the circulating band, said constant contact pressure is set as a function of at least one of said exit pressure of said measuring fluid from said nozzle, said band speed and said band tension.

3. The apparatus of claim 2, wherein said constant contact pressure corresponds at least to said exit pressure.

4. An apparatus for measuring the permeability of a circulating band in a papermaking machine, comprising:
a nozzle from which a measuring fluid flows onto the circulating band, wherein said nozzle is pressed onto the circulating band with a constant contact pressure; and
a measuring head, said nozzle being integrated in said measuring head.

5. The apparatus of claim 4, wherein said measuring head has a contact surface that is pressed onto the circulating band.

6. The apparatus of claim 4, wherein said measuring head is fabricated from an abrasion resistant material.

7. The apparatus of claim 4, wherein at least one of said measuring head is pressed against the circulating band with a specific contact pressure and said nozzle within said measuring head is additionally pressed against the circulating band independently of said specific contact pressure of said measuring head.

8. The apparatus of claim 7, wherein said specific contact pressure of said measuring head against the circulating band lies in a range approximately between 200 $N/m^2$ and 1500 $N/m^2$.

9. The apparatus of claim 4, wherein said measuring head is constructed as a frame.

10. The apparatus of claim 9, wherein said frame is provided with at least one of a plurality of sliding shoes and a plurality of rollers.

* * * * *

UNITED STATES PATENT AND TRADEMARK OFFICE
CERTIFICATE OF CORRECTION

PATENT NO. : 7,249,491 B2 Page 1 of 1
APPLICATION NO. : 10/942385
DATED : July 31, 2007
INVENTOR(S) : Ischdonat et al.

It is certified that error appears in the above-identified patent and that said Letters Patent is hereby corrected as shown below:

COLUMN 4
At line 18, please delete "is be pressed", and substitute therefore --is pressed--.

Signed and Sealed this

Twenty-ninth Day of July, 2008

JON W. DUDAS
*Director of the United States Patent and Trademark Office*